United States Patent
Zaveri et al.

(10) Patent No.: US 11,596,665 B2
(45) Date of Patent: Mar. 7, 2023

(54) SKIN LIGHTENING FORMULATIONS

(71) Applicants: Chanda Zaveri, Rancho Palos Verdes, CA (US); Meng Teng Lim, Island East (HK)

(72) Inventors: Chanda Zaveri, Rancho Palos Verdes, CA (US); Meng Teng Lim, Island East (HK)

(*) Notice: Subject to any disclaimer, the term of this patent is extended or adjusted under 35 U.S.C. 154(b) by 0 days.

(21) Appl. No.: 16/909,801

(22) Filed: Jun. 23, 2020

(65) Prior Publication Data

US 2021/0393732 A1 Dec. 23, 2021

(51) Int. Cl.

| | | |
|---|---|---|
| A61K 38/00 | (2006.01) |
| A61K 38/07 | (2006.01) |
| A61K 38/08 | (2019.01) |
| A61K 38/10 | (2006.01) |
| A61K 38/17 | (2006.01) |
| A61K 38/25 | (2006.01) |
| A61K 47/10 | (2017.01) |
| C07K 7/06 | (2006.01) |
| C07K 7/08 | (2006.01) |
| C07K 14/60 | (2006.01) |
| A61Q 19/02 | (2006.01) |
| A61Q 19/00 | (2006.01) |
| A61Q 5/02 | (2006.01) |
| A61Q 7/00 | (2006.01) |
| A61P 17/02 | (2006.01) |
| A61P 31/14 | (2006.01) |
| A61P 31/16 | (2006.01) |
| A61P 31/22 | (2006.01) |
| A61K 38/06 | (2006.01) |
| A61K 8/64 | (2006.01) |
| A61K 9/00 | (2006.01) |

(52) U.S. Cl.
CPC .............. *A61K 38/063* (2013.01); *A61K 8/64* (2013.01); *A61K 9/0014* (2013.01); *A61Q 19/02* (2013.01)

(58) Field of Classification Search
CPC .... A61K 38/00; A61K 2300/00; A61K 35/10; A61K 38/25; A61K 38/07; A61K 38/08; A61K 38/17; A61K 47/10; C07K 14/515; C07K 14/60; C07K 7/06; C07K 7/08; A61Q 19/02; A61Q 17/005; A61Q 19/00; A61Q 5/02; A61Q 7/00; A61P 17/02; A61P 31/14; A61P 31/16; A61P 31/22
See application file for complete search history.

(56) References Cited

U.S. PATENT DOCUMENTS

2012/0244094 A1* 9/2012 Farwick ................. A61Q 19/02
424/60

FOREIGN PATENT DOCUMENTS

| CH | 706226 | A2 | 9/2013 | |
|---|---|---|---|---|
| CN | 1124841 | C | 10/2003 | |
| ES | 2530140 | B1 | 12/2015 | |
| FR | 2971159 | A1 * | 8/2012 | ............. A61Q 19/00 |
| WO | WO-0168683 | A2 * | 9/2001 | ....... G01N 33/56983 |

OTHER PUBLICATIONS

Glutathione from PubChem, pp. 1-10, created on Jun. 8, 2005. (Year: 2005).*
Weschawalit et al., "Glutathione and its antiaging and antimelanogenic effcts," Clinical, Cosmetic and Investigational Dermatology, 2017, 10: 147-153. (Year: 2017).*
Mahrous, Maohmed, "Cysteamine cream," DermNet New Zealand, 2017, pp. 1-2. (Year: 2017).*
Bourgeois, Claire, "What's In Your Lotion/Potion?—Niacinamide," Aug. 23, 2016, pp. 1-5. (Year: 2016).*
International Journal of Toxicology, "Final Report of the Safety Assessment of Niacinamide and Niacin," 2005, 24(Suppl. 5): 1-31. (Year: 2005).*
FR 2971159, Machine English Translation, 1-10. (Year: 2011).*

* cited by examiner

*Primary Examiner* — Julie Ha
(74) *Attorney, Agent, or Firm* — Elevated IP, LLC

(57) ABSTRACT

Provided are pharmaceutical compositions for skin lightening, which are particularly useful in treating skin hyperpigmentation, together with methods for their use. The compositions comprise glutathione conjugated to a peptide having a sequence comprising PKEK (SEQ ID NO: 1) and cysteamine or a pharmaceutical salt thereof.

20 Claims, No Drawings

Specification includes a Sequence Listing.

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide

<400> SEQUENCE: 1

Pro Lys Glu Lys
1
```

SKIN LIGHTENING FORMULATIONS

CROSS-REFERENCE TO RELATED APPLICATIONS

None.

INCORPORATION OF SEQUENCE LISTING

This document incorporates by reference herein an electronic sequence listing text file, which was filed in electronic format via EFS-Web with the application. The text file is named "22-19_US_Seq_Listing_ST25.txt," is 349 bytes, and was created on Jun. 23, 2020.

BACKGROUND

Freckles, melasma, photoaging spots, scars, and shaving burns are among the most common hyperpigmentary conditions. Although these conditions are not harmful per se, they frequently contribute to real social, cultural, mental, and/or economic hardships, and they affect millions of people around the world. Therefore, compositions for treating hyperpigmentation are in high demand. Unfortunately, many existing formulations use harsh acids, toxic metals, and carcinogens. Given these substantial drawbacks, there is a need for new compositions that are effective, safe, easy to apply, and relatively inexpensive.

SUMMARY

The formulations and methods disclosed herein include compositions comprising (i) glutathione conjugated to a peptide that has a sequence comprising proline-lysine-glutamate-lysine (PKEK) (SEQ ID NO: 1) and (ii) cysteamine or a pharmaceutically acceptable salt of cysteamine. These formulations may be transdermally or subcutaneously delivered to a subject to stop or reverse hyperpigmentation. For example, the formulations disclosed herein may be applied to an affected area of a subject's skin in the form of a cream capable of transdermally delivering active ingredients to the epidermis, dermis, and/or hypodermis in an amount effective to cause skin lightening. Alternatively, formulations disclosed herein for reducing or eliminating hyperpigmentation may be administered to a subject by subcutaneous injection at the affected site.

In an aspect, a skin lightening formulation comprises a glutathione-PKEK (SEQ ID NO: 1) conjugate and cysteamine or a pharmaceutically acceptable salt of cysteamine.

In an aspect, a skin lightening formulation comprises a glutathione-PKEK (SEQ ID NO: 1) conjugate, cysteamine or a pharmaceutically acceptable salt of cysteamine, and niacinamide.

In an aspect, a skin lightening formulation comprises glutathione conjugated to a peptide comprising a sequence of PKEK (SEQ ID NO: 1) and cysteamine or a pharmaceutically acceptable salt of cysteamine.

In an aspect, a skin lightening formulation comprises glutathione conjugated to a peptide comprising a sequence of PKEK (SEQ ID NO: 1), cysteamine or a pharmaceutically acceptable salt of cysteamine, and niacinamide.

In an embodiment, the conjugate is present at a concentration between 2 wt. %-6 wt. %, or between 2 wt. %-5 wt. %, or between 2.5 wt. %-3.5 wt. % and the cysteamine or pharmaceutically acceptable salt of cysteamine is present at a concentration between 3 wt. %-6 wt. %, or between 3 wt. %-5 wt. %, or between 3.5 wt. %-4.5 wt. %.

In an embodiment, the formulation comprises niacinamide, which may be present at a concentration between 1 wt. %-3 wt. %, or between 1.5 wt. %-2.5 wt. %, or between 1.75 wt. %-2.25 wt. %.

In an embodiment, the formulation comprises an additional ingredient selected from the group consisting of undecylenoyl glycine, *Ascophyllum nodosum* extract, *Glycyrrhiza glabra*, *Lentinus edodes* mycelium extract, *Pisum sativum*, *Andrographis paniculata* leaf extract and combinations thereof. If present, the additional ingredient may have a concentration between 0.25 wt. %-5 wt. % or between 0.5 wt. %-3 wt. %, or between 0.5 wt. %-2 wt. %, or between 0.5 wt. %-1 wt. %.

In an embodiment, the formulation comprises one or more carriers, excipients, preservatives and/or diluents.

In an aspect, a method of reducing skin pigmentation comprises topically administering a therapeutically effective amount of a formulation disclosed herein to a subject. For example, the step of topically administering the formulation may be performed twice daily, once daily, every other day, once a week, or once a month.

In an aspect, a method of reducing skin pigmentation comprises subcutaneously injecting a therapeutically effective amount of a formulation disclosed herein at an affected area of a subject. For example, the step of subcutaneously injecting the formulation may be performed once daily, every other day, once a week, once a month, twice a year, several times a year, or once a year.

In an embodiment, a tetrapeptide (e.g., PKEK (SEQ ID NO: 1)) disclosed herein is chemically bound (e.g., covalently bound or ionically bound) to another molecule or peptide, such as glutathione, to provide one or more chemical or physical properties differing from those of the tetrapeptide alone. For example, a glutathione-tetrapeptide conjugate may provide a higher level of absorption in a subject or improved storage stability relative to the tetrapeptide alone.

DETAILED DESCRIPTION

In general, the terms and phrases used herein have their art-recognized meaning, which can be found by reference to standard texts, journal references and contexts known to those skilled in the art. The following definitions are provided to clarify their specific use in the context of this description.

An "amino acid" is a molecular building block of protein. An "amino acid residue" is the simplest discreet unit or monomer of a protein chain or peptide.

A "conjugate" is a chemical entity formed by coupling or bonding two chemical moieties. In an embodiment, a conjugate is a chemical molecule formed by covalently or ionically bonding two chemical moieties.

"Pharmaceutically acceptable salts" include both acid and base addition salts.

"Pharmaceutically acceptable acid addition salt" refers to those salts which retain the biological effectiveness and properties of the free bases and which are not biologically or otherwise undesirable, formed with inorganic acids including but not limited to hydrochloric acid, hydrobromic acid, sulfuric acid, sulfamic nitric acid, phosphoric acid and the like, and organic acids such as acetic acid, propionic acid, glycolic acid, pyruvic acid, lactic acid, oxalic acid, maleic acid, malic acid, maloneic acid, succinic acid, fumaric acid, tartaric acid, citric acid, stearic acid, ascorbic acid, benzoic acid, cinnamic acid, mandelic acid, methanesulfonic acid, ethanesulfonic acid, p-toluenesulfonic acid, salicyclic acid, naturally occurring amino acids and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine; trimethylamine, diethylamine; triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic non-toxic bases are isopropylamine, diethylamine, ethanolamine, trimethamine; dicyclohexylamine, choline, and caffeine.

Methods of Peptide Synthesis

One method of producing peptides involves chemical synthesis. This can be accomplished using solid phase methodologies well known to those skilled in the art. (See, e.g., Stewart, J. M. & Young, J. D. "Solid Phase Peptide Synthesis" Pierce Chemical Co. Rockford; Ill. 1984; Merrifield, J. Am. Chem. Soc., 85: 2149 1964; Houghten, Proc. Natl. Acad. Sci. USA 82: 5132 1985; and U.S. Pat. Nos. 4,105,603; 3,972,859; 3,842,067; and 3,862,925).

Solid phase synthesis begins at the carboxy-terminus of the putative peptide by coupling a protected amino acid to a suitable resin (e.g. chloromethylated polystyrene resin). After removal of the α-amino protecting group with, for example, trifluoroacetic acid (TFA) in methylene chloride and neutralizing in, for example TEA, the next α-amino- and sidechain protected amino acid in the synthesis is added. The remaining α-amino- and, if necessary, side-chain-protected amino acids are then coupled sequentially in the desired order by condensation to obtain an intermediate compound connected to the resin. Alternatively, some amino acids may be coupled to one another forming a peptide prior to addition of the peptide to the growing solid phase polypeptide chain.

The condensation between two amino acids, or an amino acid and a peptide, or a peptide and a peptide can be carried out according to the usual condensation methods such as the azide method, mixed acid anhydride method, DCC (N,N'-dicyclohexylcarbodiimide) or DIPC (N,N'-diisopropylcarbodiimide) methods, active ester method (p-nitrophenyl ester method), BOP benzotriazole-1-yl-oxy-tris (dimethylamino) phosphonium hexafluorophosphate method, N-hydroxysuccinic acid imido ester method, etc., and Woodward reagent K method.

Common to chemical syntheses of peptides is the protection of any reactive side-chain groups of the amino acids with suitable protecting groups. Ultimately, these protecting groups are removed after the desired polypeptide chain has been sequentially assembled. Also common is the protection of the α-amino group on an amino acid or a fragment while that entity reacts at the carboxyl group followed by the selective removal of the α-amino-protecting group to allow subsequent reaction to take place at that location. Accordingly, it is common in polypeptide synthesis that an intermediate compound is produced which contains each of the amino acid residues located in the desired sequence in the peptide chain with various of these residues having side-chain protecting groups attached. These protecting groups are then commonly removed substantially at the same time so as to produce the desired resultant product following removal from the resin.

Suitable protective groups for protecting the α- and ε-amino side chain groups are exemplified by benzyloxycarbonyl (CBZ), isonicotinyloxycarbonyl (iNOC), O-chlorobenzyloxycarbonyl (2-Cl-CBZ), p-nitrobenzyloxycarbonyl Z($NO_2$), p-methoxybenzyloxycarbonyl Z(OMe), t-butoxycarbonyl, (BOC), t-amyloxycarbonyl (AOC), isoborrnyloxycarbonyl, adamatyloxycarbonyl, 2-(4-biphenyl)-2-propyloxycarbonyl (BPOC), 9-fluorenylmethoxycarbonyl (FMOC), methylsulfonyiethoxycarbonyl (Msc), trifluoroacetyl, phthalyl, formyl, 2-nitrophenylsulphenyl (NPS), diphenylphosphinothioyl (Ppt), dimethylophosphinothioyl (Mpt) and the like.

Protective groups for the carboxy functional group are exemplified by benzyl ester (OBzl), cyclohexyl ester (Chx), 4-nitrobenzyl ester (ONb), t-butyl ester (OtBu), 4-pyridylmethyl ester (OPic), and the like. It is often desirable that specific amino acids such as arginine, cysteine, and serine possessing a functional group other than amino and carboxyl groups are protected by a suitable protective group. For example, the guanidino group of arginine may be protected with nitro, p-toluenesulfonyl, benzyloxycarbonyl, adamantyloxycarbonyl, p-methoxybenzenesulfonyl, 4-methoxy-2, 6-dimethylbenzenesulfonyl (Mds), 1,3,5-trimethylphenysulfonyl (Mts), and the like. The thiol group of cysteine may be protected with p-methoxybenzyl, triphenylmethyl, acetylaminomethyl ethylcarbamoyle, 4-methylbenzyl, 2,4, 6-trimethy-benzyl (Tmb) etc., and the hydroxyl group of serine can be protected with benzyl, t-butyl, acetyl, tetrahydropyranyl and the like.

After the desired amino acid sequence has been completed, the intermediate peptide is removed from the resin support by treatment with a reagent, such as liquid HF and one or more thio-containing scavengers, which not only cleaves the peptide from the resin, but also cleaves all the remaining side-chain protecting groups. Following HF cleavage, the peptide residue is washed with ether, and extracted from the resin by washing with aqueous acetonitrile and acetic acid.

Amino Acid Substitutions

It is a well-established principle of protein and peptide chemistry that certain amino acid substitutions, entitled "conservative" amino acid substitutions, can frequently be made in a protein or a peptide without altering either the conformation or the function of the protein or peptide. Conservative substitutions may be employed in the synthesis of proteins, peptides or analogs disclosed herein. Accordingly, peptides having conservative amino acid substitutions are within the scope of the present invention. Such changes include substituting any of isoleucine (I), valine (V), and leucine (L) for any other of these amino acids; aspartic acid (D) for glutamic acid (E) and vice versa; glutamine (O) for asparagine (N) and vice versa; and serine (S) for threonine (T) and vice versa. The above-mentioned substitutions are not the only amino acid substitutions that can be considered "conservative." Other substitutions can also be considered conservative, depending on the environment of the particular amino acid. For example, glycine (G) and alanine (A) can frequently be interchangeable, as can be alanine and valine. Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pKs of these two amino acid residues are not significant. Cysteine (C) can frequently be replaced by serine (S) when cysteine's capacity to form disulfide bonds is either undesirable or unneeded. Still other changes can be considered "conservative" in particular environments.

Pharmaceutical Compositions

Another aspect of the present invention is pharmaceutical compositions that include glutathione-PKEK (SEQ ID NO: 1) conjugates according to the present invention. In general, a pharmaceutical composition of the present invention comprises glutathione conjugated to a peptide having a sequence comprising, consisting essentially of, or consisting of PKEK (SEQ ID NO: 1) and cysteamine or a pharmaceutically acceptable salt thereof in a therapeutically effective amount and a pharmaceutically acceptable carrier, excipient or diluent.

Cysteamine, and other ingredients, may be formulated into the pharmaceutical compositions as neutral or salt forms. Pharmaceutically acceptable nontoxic salts include the acid addition salts which are formed with inorganic acids such as, for example, hydrochloric or phosphoric acids, or organic acids such as acetic, oxalic, tartaric, mandelic, and the like. Base addition salts may be derived from inorganic bases such as, for example, sodium, potassium, ammonium, calcium, or ferric hydroxides, and such organic bases as isopropyl amine, 2-ethylamino ethanol, histidine, procaine, and the like.

A therapeutically effective amount can be determined by one of ordinary skill in the art, with reference to the dosages described herein.

Conventional pharmaceutically acceptable carriers known in the art can include alcohols, e.g., ethyl alcohol, serum proteins, cholesterol, human serum albumin, liposomes, buffers such as phosphates, water, sterile saline or other salts, electrolytes, glycerol, hydroxymethylcellulose, propylene glycol, polyethylene glycol, polyexyethylenesorbitan, other surface active agents, vegetable oils, and conventional anti-bacterial or anti-fungal agents, such as parabens, chlorobutanol, phenol, sorbic acid, and the like. A pharmaceutically acceptable carrier within the scope of the present invention meets industry standards for sterility, isotonicity, stability, and non-pyrogenicity.

The active ingredient is often mixed with diluents or excipients that are physiologically tolerable and compatible with the active ingredient. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH-buffering agents, and the like. For a more detailed description of the foregoing see a standard pharmaceutical text such as Remington's Pharmaceutical Sciences, Mack Publishing Co. Easton, Pa. (1970).

Methods of Use and Administration

The compounds of this invention are shown to reduce or eliminate skin hyperpigmentation. Skin lightening formulations according to the present invention can be administered by a number of routes including but not limited to topical and subcutaneous administration.

The dosages to be administered can be determined by one of ordinary skill in the art depending on the clinical severity of the disease, the age, sex and weight of the patient, the exposure of the patient to conditions that may affect the course of treatment (e.g., sunlight), the existence or nonexistence of underlying systemic problems such as diabetes, impaired circulation, and immunocompromised status, and other pharmacokinetic factors generally understood in the art, such as liver and kidney metabolism. The interrelationship of dosages for animals of various sizes and species and humans based on mg/m$^3$ of surface area is described by E. J. Freireich et al., "Quantitative Comparison of Toxicity of Anticancer Agents in Mouse, Rat, Hamster; Dog, Monkey and Man," Cancer Chemother. Rep. 50:219-244 (1966). Adjustments in the dosage regimen can be made to optimize the therapeutic response. Doses can be divided and administered on a daily basis or the dose can be reduced proportionally depending on the therapeutic situation.

Methods according to the present invention can be used to treat humans or socially or economically important animal species. Methods according to the present invention are not limited to use in humans.

The invention is illustrated by the following Examples. These Examples are for illustrative purposes only and are not intended to limit the invention.

Example 1: Skin Lightening Preparations

This Example describes primary ingredients for skin lightening formulations. Typically, deionized water is the main carrier for the ingredients.

TABLE 1

Skin lightening formulation ingredients.

| Ingredients | Concentration (wt. %) |
|---|---|
| Glutathione-PKEK (SEQ ID NO: 1) conjugate | 2-6 |
| Cysteamine HCl | 3-6 |

Example 2: Light Perfecting Restorative Cream

This Example describes a skin lightening cream comprising the ingredients shown in Table 1 and other ingredients.

TABLE 2

Skin lightening cream ingredients.

| No. | Ingredient | Concentration (wt. %) |
|---|---|---|
| 1 | Deionized water | qs |
| 2 | Isopropyl myristate | 4 |
| 3 | Cysteamine HCl | 4 |
| 4 | Niacinamide | 2 |
| 5 | Glycerine | 2 |
| 6 | Glyceryl stearate SE | 2 |
| 7 | Behentrimonium methosulfate | 1 |
| 8 | Glutathione/Tetrapeptide Pro-Lys-Glu-Lys | 3 |
| 9 | PEG-100 stearate | 1 |
| 10 | Cetyl hydroxyethylcellulose | 1 |
| 11 | Cetyl alcohol | 1 |
| 12 | Polysorbate-20 | 1 |
| 13 | Tocophery acetate | 1 |
| 14 | Ascophyllum nodosum extract | 0.5 |
| 15 | Glycyrrhiza glabra | 0.5 |
| 16 | Lentinus edodes mycelium extract | 0.5 |
| 17 | Pisum sativum | 0.5 |
| 18 | 3-0 Ethyl ascorbic acid | 0.5 |
| 19 | Phenylethyl resorcinol | 0.5 |
| 20 | Andographis paniculata leaf extract | 0.5 |
| 21 | Phenoxyethanol | 0.5 |
| 22 | Ethylhexylglycerin | 0.5 |
| 23 | Caprylyl glycol | 0.5 |
| 24 | Hexylene glycol | 0.5 |

Example 3 Underarm Skin Whitening Cream

With repetitive shaving and depilatory treatments, the skin of the armpit area often becomes darker and thicker. This Example describes an underarm skin whitening/lightening cream comprising the ingredients shown in Table 1 and other ingredients.

TABLE 3

Underarm skin whitening/lightening cream ingredients.

| No. | Ingredient | Concentration (wt. %) |
|---|---|---|
| 1 | Deionized water | qs |
| 2 | Isopropyl myristate | 4 |
| 3 | Cysteamine HCl | 4 |
| 4 | Niacinamide | 2 |
| 5 | Glycerine | 2 |
| 6 | Glyceryl stearate SE | 2 |
| 7 | Behentrimonium methosulfate | 1 |
| 8 | Glutathione/Tetrapeptide Pro-Lys-Glu-Lys | 3 |
| 9 | Glyceryl stearate | 2 |
| 10 | PEG-100 stearate | 1 |
| 11 | Cetyl hydroxyethylcellulose | 1 |
| 12 | Cetyl alcohol | 1 |
| 13 | Polysorbate-20 | 1 |
| 14 | Tocopheryl acetate | 1 |
| 15 | Undecylenoyl glycine (Lipacide UG) | 3 |
| 16 | Ascophyllum nodosum extract | 0.5 |
| 17 | Glycyrrhiza glabra | 0.5 |
| 18 | Lentinus edodes mycelium extract | 0.5 |
| 19 | Pisum sativum | 0.5 |
| 20 | 3-0 Ethyl ascorbic acid | 0.5 |
| 21 | Phenylethyl resorcinol | 0.5 |
| 22 | Andrographis paniculata leaf extract | 0.5 |
| 23 | Phenoxyethanol | 0.5 |
| 24 | Ethylhexylglycerin | 0.5 |
| 25 | Caprylyl glycol | 0.5 |
| 26 | Hexylene glycol | 0.5 |

Example 4: Skin Whitening Cream

This Example describes a skin whitening/lightening cream comprising the ingredients shown in Table 1 and other ingredients.

TABLE 4

Skin whitening cream ingredients.

| No. | Ingredient | Concentration (wt. %) |
|---|---|---|
| 1 | Deionized water | qs |
| 2 | Isopropyl myristate | 4 |
| 3 | Cysteamine HCl | 4 |
| 4 | Niacinamide | 2 |
| 5 | Glycerine | 2 |
| 6 | Glyceryl stearate SE | 2 |
| 7 | Behentrimonium methosulfate | 1 |
| 8 | Glutathione/Tetrapeptide Pro-Lys-Glu-Lys | 3 |
| 9 | PEG-100 stearate | 1 |
| 10 | Glycerol stearate | 2 |
| 11 | Cetyl hydroxyethylcellulose | 1 |
| 12 | Cetyl alcohol | 1 |
| 13 | Polysorbate-20 | 1 |
| 14 | Tocopheryl acetate | 1 |
| 15 | Undecylenoyl glycine (Lipacide UG) | 3 |
| 16 | Ascophyllum nodosum extract | 0.5 |
| 17 | Glycyrrhiza glabra | 0.5 |
| 18 | Lentinus edodes mycelium extract | 0.5 |
| 19 | Pisum sativum | 0.5 |
| 20 | 3-0 Ethyl ascorbic acid | 0.5 |
| 21 | Phenylethyl resorcinol | 0.5 |
| 22 | Andrographis paniculata leaf extract | 0.5 |
| 23 | Phenoxyethanol | 0.5 |
| 24 | Ethylhexylglycerin | 0.5 |

Example 5: Method of Making Skin Whitening Cream

An exemplary method of making a skin whitening cream involves combining all ingredients in a single vessel and blending with a paddle, whisk, or rotary screw at medium to high speed for between 5 minutes and 1 hour until a substantially homogeneous mixture is formed.

STATEMENTS REGARDING INCORPORATION BY REFERENCE AND VARIATIONS

All references cited throughout this application, for example patent documents including issued or granted patents or equivalents; patent application publications; and non-patent literature documents or other source material; are hereby incorporated by reference herein in their entireties, as though individually incorporated by reference.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments, exemplary embodiments and optional features, modification and variation of the concepts herein disclosed can be resorted to by those skilled in the art, and that such modifications and variations are considered to be within the scope of this invention as defined by the appended claims. The specific embodiments provided herein are examples of useful embodiments of the invention and it will be apparent to one skilled in the art that the invention can be carried out using a large number of variations of the devices, device components, and method steps set forth in the present description. As will be apparent to one of skill in the art, methods and devices useful for the present methods and devices can include a large number of optional composition and processing elements and steps.

When a group of substituents is disclosed herein, it is understood that all individual members of that group and all subgroups are disclosed separately. When a Markush group or other grouping is used herein, all individual members of the group and all combinations and subcombinations possible of the group are intended to be individually included in the disclosure.

It must be noted that as used herein and in the appended claims, the singular forms "a", "an", and "the" include plural reference unless the context clearly dictates otherwise. Thus, for example, reference to "a peptide" includes a plurality of such peptides and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are described. Nothing herein is to be construed as an admission that the invention is not entitled to antedate such disclosure by virtue of prior invention.

Whenever a range is given in the specification, for example, a range of integers, a temperature range, a time range, a composition range, or concentration range, all intermediate ranges and subranges, as well as all individual values included in the ranges given are intended to be included in the disclosure. As used herein, ranges specifically include the values provided as endpoint values of the range. As used herein, ranges specifically include all the integer values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous and can be used interchangeably with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" can be replaced with either of the other two terms. The invention illustratively described herein suitably can be practiced in the absence of any element or elements, limitation or limitations which is/are not specifically disclosed herein.

All art-known functional equivalents of materials and methods are intended to be included in this disclosure. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments and optional features, modification and variation of the concepts herein disclosed can be resorted to by those skilled in the art, and that such modifications and variations are considered to be within the scope of this invention as defined by the appended claims.

What is claimed is:

1. A skin lightening formulation comprising:
a glutathione-PKEK (SEQ ID NO: 1) conjugate; and
cysteamine or a pharmaceutically acceptable salt of cysteamine.

2. The formulation of claim 1, wherein the conjugate is present at a concentration between 2 wt. %-6 wt. % and the cysteamine is present at a concentration between 3 wt. %-6 wt. %.

3. The formulation of claim 1, further comprising niacinamide.

4. The formulation of claim 3, wherein the niacinamide is present at a concentration between 1 wt. %-3 wt. %.

5. The formulation of claim 1, further comprising an additional ingredient selected from the group consisting of undecylenoyl glycine, *Ascophyllum nodosum* extract, *Glycyrrhiza glabra, Lentinus edodes* mycelium extract, *Pisum sativum, Andrographis paniculata* leaf extract and combinations thereof.

6. The formulation of claim 5, wherein the additional ingredient is present at a concentration between 0.25 wt. %-5 wt. %.

7. The formulation of claim 1, further comprising one or more carriers, excipients, preservatives and/or diluents.

8. A skin lightening formulation comprising:
a glutathione-PKEK (SEQ ID NO: 1) conjugate;
cysteamine or a pharmaceutically acceptable salt of cysteamine; and
niacinamide.

9. The formulation of claim 8, wherein the conjugate is present at a concentration between 2 wt. %-6 wt. %, the cysteamine is present at a concentration between 3 wt. %-6 wt. %, and the niacinamide is present at a concentration between 1 wt. %-3 wt. %.

10. The formulation of claim 8, further comprising an additional ingredient selected from the group consisting of undecylenoyl glycine, *Ascophyllum nodosum* extract, *Glycyrrhiza glabra, Lentinus edodes* mycelium extract, *Pisum sativum, Andrographis paniculata* leaf extract and combinations thereof.

11. The formulation of claim 10, wherein the additional ingredient is present at a concentration between 0.25 wt. %-5 wt. %.

12. The formulation of claim 8, further comprising one or more carriers, excipients, preservatives and/or diluents.

13. A skin lightening formulation comprising:
glutathione conjugated to a peptide comprising a sequence of PKEK SEQ ID NO: 1); and
cysteamine or a pharmaceutically acceptable salt of cysteamine.

14. The formulation of claim 13, further comprising niacinamide.

15. The formulation of claim 14, wherein the conjugate is present at a concentration between 2 wt. %-6 wt. %, the cysteamine is present at a concentration between 3 wt. %-6 wt. %, and the niacinamide is present at a concentration between 1 wt. %-3 wt. %.

16. The formulation of claim 13, further comprising an additional ingredient selected from the group consisting of undecylenoyl glycine, *Ascophyllum nodosum* extract, *Glycyrrhiza glabra, Lentinus edodes* mycelium extract, *Pisum sativum, Andrographis paniculata* leaf extract and combinations thereof.

17. The formulation of claim 16, wherein the additional ingredient is present at a concentration between 0.25 wt. %-5 wt. %.

18. The formulation of claim 16, further comprising one or more carriers, excipients, preservatives and/or diluents.

19. A method of reducing skin pigmentation in a subject, said method comprising topically administering to said subject a therapeutically effective amount of the formulation of claim 1.

20. The method of claim 19, wherein the step of topically administering the formulation is performed twice daily, once daily, every other day, once a week or once a month.

* * * * *